United States Patent [19]
Renz

[11] Patent Number: 5,723,030
[45] Date of Patent: Mar. 3, 1998

[54] ELECTROCHEMICAL MEASURING SENSOR AND METHOD FOR MAKING THE SAME

[75] Inventor: Hans-Joerg Renz, Leinfelden-Echterdingen, Germany

[73] Assignee: Robert Bosch GmbH, Stuttgart, Germany

[21] Appl. No.: 628,704

[22] PCT Filed: Oct. 10, 1995

[86] PCT No.: PCT/DE95/01387

§ 371 Date: Apr. 16, 1996

§ 102(e) Date: Apr. 16, 1996

[87] PCT Pub. No.: WO96/14574

PCT Pub. Date: May 17, 1996

[30] Foreign Application Priority Data

Nov. 8, 1994 [DE] Germany ............... 44 39 898.0

[51] Int. Cl.[6] ............................................. G01N 27/26
[52] U.S. Cl. ..................... 204/427; 204/424; 204/425
[58] Field of Search ............................... 204/424–429

[56] References Cited

U.S. PATENT DOCUMENTS 4,174,258   11/1979   Bode ............................ 204/429

*Primary Examiner*—Bruce F. Bell
*Attorney, Agent, or Firm*—Spencer & Frank

[57] ABSTRACT

An electrochemical measuring sensor for determining the oxygen content of gases, in particular, for determining the oxygen content in exhaust gases of internal combustion engines, with the sensor having a tube-shaped sensor element at whose outer side a measuring electrode is arranged which is exposed to the measuring gas and at whose inner side a reference electrode is arranged which is exposed to a reference gas. A pumping reference volume (58) is allocated to the reference electrode (36), which pumping reference volume is coated with a layer (60) having a high gas diffusion resistance.

15 Claims, 2 Drawing Sheets

ELECTROCHEMICAL MEASURING SENSOR AND METHOD FOR MAKING THE SAME

BACKGROUND OF THE INVENTION

This application is a 371 of PCT/DE95/01387 filed Dec. 10, 1995.

The invention relates to an electrochemical measuring sensor for determining the oxygen content of gases, in particular, for determining the oxygen content in exhaust gases of internal combustion engines, having a tube-shaped sensor element formed of a solid electrolyte at whose outer side a measuring electrode is arranged which is exposed to the measuring gas and at whose inner side a reference electrode is arranged to a method for making the measuring sensor.

PRIOR ART

Electrochemical measuring sensors of the generic type are known. These are embodied, for example, in a so-called finger design, wherein a solid electrolyte body forms a sensor element which, as a closed tube, is tightly fixed in a metallic housing. Here, an outer measuring electrode of the sensor element is directly exposed to the gas to be measured, whereas an inner electrode serving as reference electrode is exposed to a reference gas, for example, the atmospheric oxygen. The electrodes are connected to an evaluation circuit via conductor tracks which, on the inside and on the outside, are guided on the closed tube. If the measuring electrode is acted upon by a gas to be measured, for example, by the exhaust gas of a motor vehicle, a different partial oxygen pressure appears at the measuring electrode and at the reference electrode so that a voltage signal can be tapped between the electrodes. This voltage signal serves to determine the oxygen content in the exhaust gas so that conclusions can be drawn regarding the operation of the internal combustion engine. Particularly the so-called lambda value can be determined which represents a measure for the composition of the air-fuel mixture with which the internal combustion engine is operated. Depending on whether it is the air or the fuel that is present in stoichiometric excess, the lambda value is larger or smaller than 1.

The known electrochemical measuring sensors have in common that they are directly exposed to the exhaust gas path so that the reference electrode needs to be sufficiently sealed vis-a-vis the exhaust gas path. For this purpose it is known to arrange a plurality of special seals which allow, on the one hand, a sealing of the reference electrode against the exhaust gas and, on the other hand, a supply of the reference gas, namely of the atmospheric oxygen, to the reference electrode. The seal arrangements have a complicated and complex design. Unburnt fuel reaches the exhaust gas path practically washing around the measuring sensor particularly during specific operating situations of the motor vehicle, for example, during startup, which means that even for gastight seals it cannot be excluded that the fuel enters the reference region.

SUMMARY AND ADVANTAGES OF THE INVENTION

In contrast to the known measuring sensors, the measuring sensor according to the invention for determining the oxygen content of gases, in particular, for determining the oxygen content in exhaust gases of internal combustion engines, has a tube-shaped sensor element formed of a solid electrolyte at whose outer side a measuring electrode is arranged which is exposed to the measuring gas and at whose inner side a reference electrode is arranged, and wherein the reference electrode is coated with a ceramic layer having a high gas diffusion resistance such that a pumping reference volume forms at the reference electrode. The measuring sensor according to the invention offers the advantage that a sealing of the reference electrode is possible in a simple manner. Since the reference electrode is allocated a pumping reference volume covered with a layer having a high gas diffusion resistance, it is possible in a simple manner to limit the sealing of the reference electrode to the layer that covers the pumping reference volume. The pumping reference volume forms an internal oxygen supply source for the reference electrode. By applying a pumping voltage to the reference electrode and a measuring electrode that is exposed to the measuring gas, the pumping reference volume can be constantly supplied with fresh oxygen ions from the measuring gas. Thus, a connection of the pumping reference volume to the atmosphere and to the seals thus required to prevent the penetration of foreign substances, for example, of fuels, can be saved. The reference pumping voltage is constantly present at the sensor element and is superposed by the appearing voltage signal because of a difference in oxygen concentration in the measuring gas, namely at the measuring electrode, and in the pumping reference volume, namely at the reference electrode. By means of an evaluation circuit, the pumping reference voltage signal can be aligned in a simple manner with the measuring voltage signal so that a signal is available which corresponds to the oxygen concentration differential.

In an advantageous embodiment of the invention it is provided that the pumping reference volume is arranged at a base of the sensor element and is lidded by the layer which is preferred to not be 100% impermeable to gas. In this manner it is accomplished that the layer covering the pumping reference volume can assume a valve function at the same time which is activated in the event that an oxygen concentration develops in the pumping reference volume that is too high due to the pumping reference voltage signal which is constantly present. An excess pressure that develops here is reduced via the layer covering the pumping reference volume when a specific limit value is reached.

Furthermore, it is advantageous that the pumping reference volume and/or the layer covering the pumping reference volume are comprised of the same material as the sensor element. Preferably, a function of the pumping reference volume and of the layer covering the pumping reference volume is set by selecting a different porosity. Thus, the design of the measuring sensor is possible in a simple manner by way of the generally known process steps which can be mastered technologically.

The object is further solved according to the invention by in a method for making an electrochemical measuring sensor for determining the oxygen content of gases, in particular, for determining the oxygen content in exhaust gases of internal combustion engines, which measuring censor has a tube-shaped sensor element of a solid electrolyte at whose outer side a measuring electrode is arranged which is exposed to the measuring gas and at whose inner side a reference electrode is arranged which is exposed to a reference gas, with the method including applying a pumping reference volume and a ceramic layer covering the pumping reference volume on the reference side of the sensor element. Since, on the reference side of the tube-shaped sensor element, a pumping reference volume and a layer covering the pumping reference volume are applied, which preferably takes place by way of a defined instillation of a material resulting in the pumping reference volume and the layer, it is possible in a simple manner to provide the tube-shaped sensor element with a sealed pumping reference volume. Because of the pot-shaped form of the tube-shaped sensor element, the material which results in the pumping reference volume can be instilled in a simple manner into the sensor element in a continuous operation so that, by means of a metered addition of a specific amount of the material, a defined pumping reference volume can be generated in the sensor element.

The generated pumping reference volume can preferably be covered with a further instilled material layer which, compared to the pumping reference volume, is provided with a high gas diffusion resistance. The materials resulting in the pumping reference volume and the layer covering the pumping reference volume may be cosintered together with the sensor element so that a complete sensor element can be made in a single process step. The processes for the placing-in of the pumping reference volume and the layer covering the pumping reference volume can thus be combined with the known process steps for making the sensor elements and they are suitable for mass-production.

Further advantageous embodiments ensue from the remaining features which are mentioned in the dependent claims.

BRIEF DESCRIPTION OF THE DRAWINGS

In the following, the invention is explained in greater detail in an embodiment by way of the associated drawings, wherein.

DETAILED DESCRIPTION OF THE PREFERRED EMBODIMENT

Figure 1:
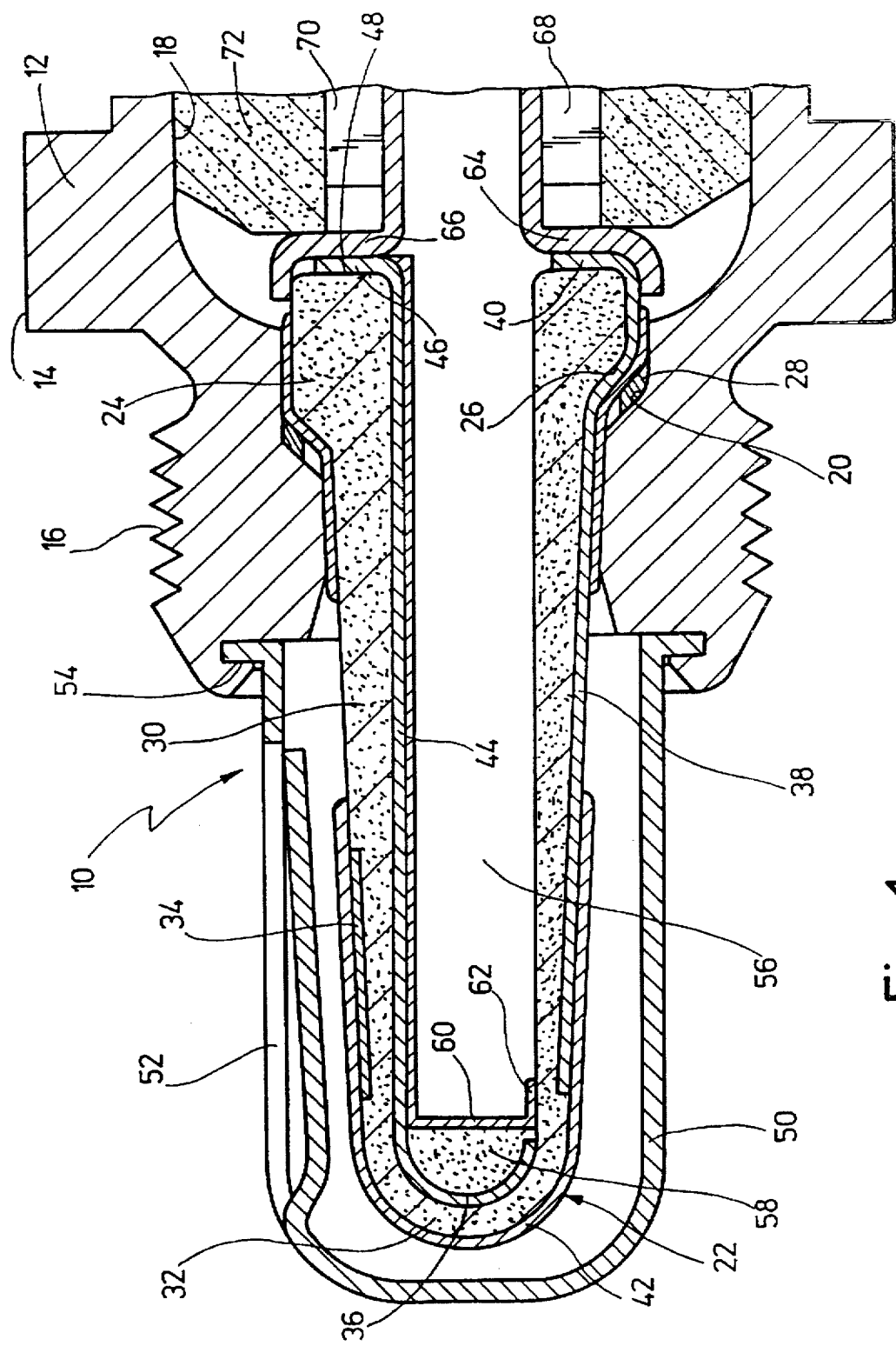
FIG. 1 is a sectional representation through an electrochemical measuring sensor.

FIG. 1 shows, in a sectional representation, an electrochemical measuring sensor which is identified in general by 10. The measuring sensor 10 has a metallic housing 12 provided at its outer side with a hexagonal wrench shape 14 and with a winding 16 for the fastening in a measuring gas tube, not shown. The housing 12 has a sleeve-shaped configuration and is provided with a through-opening 18. The through-opening 18 is embodied as a stepped bore and forms a tight seat 20. A sensor element 22 is guided in the through-opening 18 of the housing 12. The sensor element 22 has a toric head 24 which forms an annular shoulder 26. A seal 28 is arranged between the sensor element 22 and the housing 12.

The measuring sensor 10 shown in FIG. 1 has a sensor element 22 which is arranged so as to be potential-free, with the fundamental design also being valid for a sensor element 22 which is affected by potential. The differences that exist between the sensor elements 22 arranged to be potential-free and those that are affected by potential will not be explained in greater detail within the framework of the present description since the person skilled in the art is familiar with them in general.

In the present example, the sensor element 22 is an oxygen probe known per se which is preferably used for measuring the partial oxygen pressure in exhaust gases, preferably in motor vehicles. The sensor element 22 has a tube-shaped solid electrolyte body 30 whose end section on the measuring gas side is closed by means of a bottom 32.

A layer-shaped, gas-permeable measuring electrode 34 is arranged on the outer side of the solid electrolyte body 30 exposed to the measuring gas. A gas-permeable reference electrode 36, which is also layer-shaped, is arranged on the inner side of the solid electrolyte body facing away from the outer side. The measuring electrode 34 is connected to a first electrode contact 40 by way of a conductor track 38. A porous protective layer 42 is placed over the measuring electrode 34 and partially over the conductor track 38. The reference electrode 36 is connected to a second electrode contact 46 by way of a second conductor track 44. The electrode contacts 40 and 46 are respectively disposed on an end face 48 formed by the open end of the solid electrolyte body 30. The conductor tracks 38 and 44 are preferably configured as cermet layers and are cosintered.

The sensor element 22 protruding from the through-opening 18 of the housing 12 on the measurement gas side is surrounded at a distance by a protective tube 50 which is provided with openings 52 so that a measuring gas can enter or escape. The protective tube 50 is held at the measuring gas end of the housing 12, for example, fitted into a groove 54.

A pumping reference volume 58 is arranged in an interior chamber 56 of the solid electrolyte body 30 above the reference electrode 36. The pumping reference volume 58 is comprised of a ceramic material which is provided with a porosity for taking up a reference gas. The pumping reference volume 58 may be comprised, for example, of the same material as the solid electrolyte body 30. The solid electrolyte body 30 as well as the pumping reference volume 58 may be comprised, for example, of stabilized zirconium oxide. A porosity may result from admixing the stabilizing agents, for example, yttrium oxide. By adding different amounts of stabilizers and/or further components that are dissolved during a sintering process, the porosity of the solid electrolyte body 30 as well as of the pumping reference volume 58 can be set. The pumping reference volume 58 is embodied approximately hemispherically and fills the interior chamber 56 of the solid electrolyte body 30 in the region of its bottom 32. A layer 60 is arranged above the pumping reference volume 58. The layer 60 covers the pumping reference volume 58 over its entire surface facing the interior chamber. At its outside circumference, the layer 60 forms a collar 62 which stands up in the direction of the end of the solid electrolyte body 30 that is disposed away from the measuring gas. Furthermore, the layer 60 is arranged above the conductor track 44 connecting the reference electrode 36 with the electrode contact 46. Here, the layer 60 is preferably provided only in the region of the conductor track 44, that is, not over the entire inside circumference of the solid electrolyte body 30. Preferably, the layer 60 is also comprised of a ceramic material having a high gas diffusion resistance. Zirconium oxide, for example, may again be used as material for the layer 60, with it being possible to set the gas diffusion resistance by way of suitable stabilizers.

A first contact element 64 lies on the first electrode contact 40 and a second contact element 66 on the second electrode contact 46. The contact elements 64 and 66 are connected with a measuring electrode connection 68 and a reference electrode connection 70. The connections 68 and 70 are connected with connection cables, not shown, and are guided to the outside to a measuring or control device.

Furthermore, an insulating sheath 72 is placed into the through-opening 18 of the housing 12, which sheath is preferably comprised of a ceramic material. With the assistance of a mechanical means, not shown, the insulating sheath 72 is pressed onto the contact elements 64 and 66, whereby an electrical connection to the electrode contacts 40 and 46 is realized.

In the remaining interior chamber 56 of the solid electrolyte body 30, a heating device can furthermore be provided which is not shown here.

Figure 2:
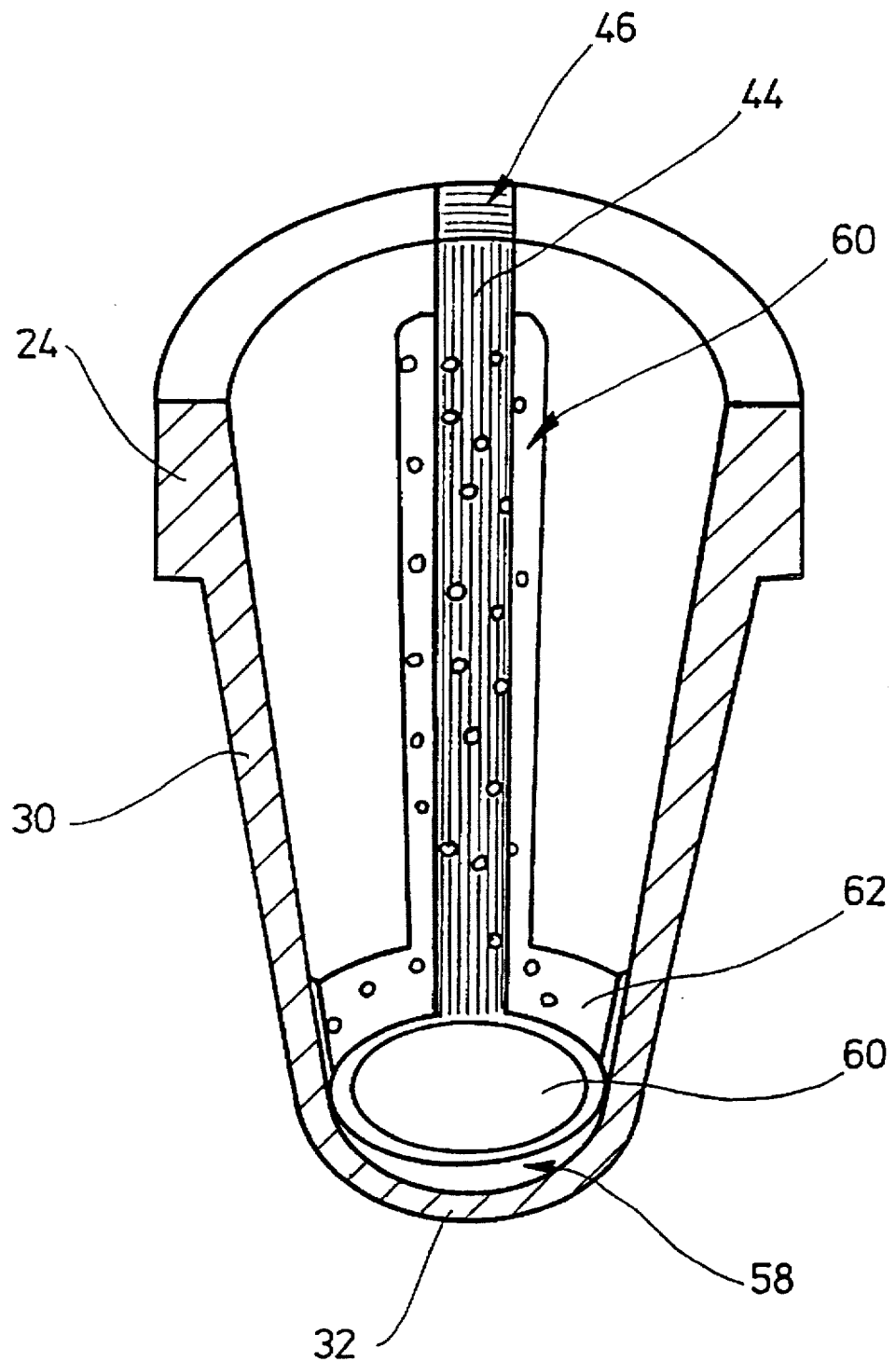
FIG. 2 is a perspective sectional representation through a sensor element according to the invention.

FIG. 2 is a schematic perspective view of the solid electrolyte body 30 which has been cut open. Elements that are identical to those in FIG. 1 are provided with identical reference numerals and are not explained again. By way of the perspective view it becomes clear how the pumping reference volume 58 is arranged in the hollow chamber 56 at the bottom 32 of the solid electrolyte body 30. The pumping reference volume 58 completely covers the reference electrode 36 which is not shown in FIG. 2. The layer 60 is provided above the pumping reference volume 58, which layer ends in the collar 62 on the one hand and covers the conductor track 44 on the other.

The measuring sensor 10 shown in FIGS. 1 and 2 has the following function:

Via the connections 68 and 70 or the conductor tracks 38 and 44, a pumping voltage signal which is set in a defined manner is applied between the measuring electrode 34 and the reference electrode 36. The pumping voltage signal is made available by the measuring or control device which is not shown. Because of the pumping voltage that is present, oxygen ions are pumped into the pumping reference volume 58 out of the measuring gas which can enter the housing 50 through the openings 52. The process of pumping oxygen ions out of a measuring gas into a pumping reference is commonly known. If an oxygen concentration in the measuring gas changes, the partial oxygen pressure at the measuring electrode 34 also changes compared to the partial oxygen pressure at the reference electrode 36. In this manner, a specific voltage signal can be tapped which is proportional to the oxygen concentration differential between the measuring electrode 34 and the reference electrode 36. This voltage signal is aligned with the pumping voltage signal in an evaluation circuit of the measuring or control devices, not shown, so that a measuring signal is obtained which is a measure for an oxygen concentration in the measuring gas. This can be used in a commonly known manner for the control of an injection of an internal combustion engine of a motor vehicle.

The layer 60 arranged above the pumping reference volume 58 ensures that foreign substances, in particular benzene vapors or liquid fuel, cannot penetrate into the pumping reference volume 58. The configuration of the collar 62 and the presence of the layer 60 above the conductor track 44 prevent fuel or fuel vapors from penetrating into the pumping reference volume 58. By embodying the layer 60, a sealing of the interior chamber 56 against fuels or fuel vapors must no longer meet any particular demand. This means that the arrangement of additional, expensive sealing elements, which furthermore must ensure a sealing leadthrough of the connections 68 and 70, is no longer absolutely necessary.

By setting a defined high gas diffusion resistance of the layer 60, a valve function for the pumping reference volume 58 becomes possible in addition to the sealing of the pumping reference volume 58 against fuels or fuel vapors. If, as a result of the pumping-in of oxygen ions, the pressure within the pumping reference volume 58 increases because of the permanently applied pumping voltage between the measuring electrode 34 and the reference electrode 36, this pressure can be reduced by the layer 60 when a predeterminable limit value is reached. The limit values can be set by means of a porosity of the layer 60, which porosity simultaneously determines the gas diffusion resistance of the layer 60. Thus, the sensor element 22 is at the same time protected against destruction caused by excessive pressures within the pumping reference volume 58.

The sensor element 22 can be made in that, following the application of the reference electrode 36 and of the conductor track 44 connecting the reference electrode with the electrode contact 46, the material resulting in the pumping reference volume 58 is filled into the hollow chamber 56 of the solid electrolyte body 30 through the opening shown in FIG. 1 which is disposed away from the measuring gas. Filling may take place, for example, by instillation of a ceramic material. The amount of ceramic material is such that the filling takes place until a filling level within the solid electrolyte body 30 is reached which ensures that the reference electrode 36 is covered. A further option is to completely fill the hollow chamber 56 of the solid electrolyte body 30 with the ceramic material and to then take out, for example, remove by suction, this ceramic material until the filling level is reached that is required for the pumping reference volume 58.

The ceramic mass resulting in the layer 60 is then applied on top of the ceramic mass resulting in the pumping reference volume 58. The layer 60 can also be applied, for example, by means of defined instillation of a specific amount of ceramic material. The placing-in of the layer 60 can also occur, for example, by placing in an already prefabricated film having the contours of the layer 60 including its collar 62 and of the components straddling the conductor track 44. Stabilizers which allow the setting of a defined porosity are mixed in with the ceramic material resulting in the pumping reference volume 58 and with the ceramic material resulting in the layer 60. This takes place in such a manner that the pumping reference volume 58 is suitable for storing the oxygen, whereas the layer 60 forms an impermeable barrier for fuels or fuel vapors. The layer 60 permits oxygen to escape from the pumping reference volume 58 into the interior chamber 56 of the sensor element 22 when a specific limit pressure value is reached in that the layer has a clearly defined, high gas diffusion resistance. After placing in the ceramic material resulting in the pumping reference volume 58 or the ceramic material resulting in the layer 60, the sensor element 22 can be sintered. Here, sintering can take place, for example, as so-called cosintering in that the solid electrolyte body 30, the pumping reference volume 58 and the layer 60 are sintered in one process step. Consecutive sintering is also possible, however, in that, for example, the solid electrolyte body 30 is first sintered with the measuring electrode 34, the reference electrode 36 and the conductor tracks 38 or 34 and that the pumping reference volume 58 and the layer 60 are sintered on only afterwards. The sintering of ceramic materials is commonly known and will not be explained in further detail within the framework of the description.

What is claimed is:

1. An electrochemical measuring sensor for determining the oxygen content of gases, said measuring sensor having a tube-shaped sensor element at whose outer side a measuring electrode is arranged which is exposed to a measuring gas and at whose inner side a reference electrode is arranged, wherein the reference electrode is covered with a layer having a high gas diffusion resistance such that a pumping reference volume forms at the reference electrode, and wherein at its outside circumference, the layer forms a collar on an inside wall of the sensor element.

2. An electrochemical measuring sensor for determining the oxygen content of gases, said measuring sensor having a tube-shaped sensor element at whose outer side a measuring electrode is arranged which is exposed to a measuring gas and at whose inner side a reference electrode is arranged, wherein the reference electrode is covered with a layer having a high gas diffusion resistance such that a pumping reference volume forms at the reference electrode, and wherein the pumping reference volume is arranged at the bottom of the sensor element and is lidded with the layer.

3. Measuring sensor according to claim 1, wherein the layer simultaneously covers a conductor track which connects the reference electrode.

4. Measuring sensor according to claim 2, wherein, at its outside circumference, the layer forms a collar on an inside wall of the sensor element.

5. Measuring sensor according to claim 2, wherein at least one of the pumping reference volume and the layer is comprised of the same material as the sensor element.

6. Measuring sensor according to claim 2, wherein of the ceramic material employed for the sensor element, the pumping reference volume and the layer have different porosities to set their respective functions.

7. Measuring sensor according to claim 2, further including a means for applying a permanent pumping voltage signal to the reference electrode and the measuring electrode so that a pumping of oxygen ions into the pumping reference volume takes place.

8. Method for making an electrochemical measuring sensor for determining the oxygen content of gases, with the sensor having a tube-shaped sensor element at whose outer side a measuring electrode is arranged which is exposed to a measuring gas and at whose inner side a reference electrode is arranged which is exposed to a reference gas, said method including forming a pumping reference volume and a layer on a reference side of the sensor element.

9. Method according to claim 8, including forming the pumping reference volume and the layer covering the pumping reference volume prior to sintering of the sensor element.

10. Method according to claim 8, including forming the pumping reference volume and the layer covering the pumping reference volume by placing some into an interior chamber of the tube-shaped sensor element.

11. Method according to claim 10, including forming the pumping reference volume and the layer covering the pumping reference volume by filling a defined amount of a ceramic material into the interior chamber.

12. Method according to claim 8, including forming the pumping reference volume and the layer covering the pumping reference volume by the instillation of a defined amount of a ceramic material.

13. Method according to claim 8, including forming the pumping reference volume and the layer covering the pumping reference volume by filling-in an arbitrary amount of a ceramic material and by a subsequent defined removal by suction of an excess amount of the ceramic material that was filled in.

14. Method according to claim 8, wherein the pumping reference volume and the layer covering the pumping reference volume are cosintered with the sensor element.

15. Method according to claim 8, characterized in that the sensor element, the pumping reference volume and the layer covering the pumping reference volume are sintered in separate steps.

* * * * *